US009683260B2

(12) United States Patent
Georgiou et al.

(10) Patent No.: US 9,683,260 B2
(45) Date of Patent: Jun. 20, 2017

(54) CHEMICAL SENSING DEVICE

(75) Inventors: Pantelis Georgiou, Wembley Middlesex (GB); Sam Reed, London (GB); Yan Liu, London (GB); Christofer Toumazou, London (GB); Chung-Pei Ou, Singapore (SG)

(73) Assignee: DNAE GROUP HOLDINGS LIMITED, London (GB)

( * ) Notice: Subject to any disclaimer, the term of this patent is extended or adjusted under 35 U.S.C. 154(b) by 1063 days.

(21) Appl. No.: 13/881,986

(22) PCT Filed: Oct. 28, 2011

(86) PCT No.: PCT/GB2011/052105
§ 371 (c)(1),
(2), (4) Date: Apr. 26, 2013

(87) PCT Pub. No.: WO2012/056247
PCT Pub. Date: May 3, 2012

(65) Prior Publication Data
US 2013/0252828 A1  Sep. 26, 2013

(30) Foreign Application Priority Data
Oct. 28, 2010  (GB) .................................. 1018224.4

(51) Int. Cl.
*G01N 15/06* (2006.01)
*G01N 33/00* (2006.01)
(Continued)

(52) U.S. Cl.
CPC ......... *C12Q 1/6874* (2013.01); *C12Q 1/6825* (2013.01); *C12Q 1/6858* (2013.01); *G01N 27/4145* (2013.01); *G01N 27/44* (2013.01)

(58) Field of Classification Search
CPC ........ G01N 15/06; G01N 33/00; G01N 33/48;
G01N 27/00
(Continued)

(56) References Cited

U.S. PATENT DOCUMENTS 4,478,914 A * 10/1984 Giese ........................... 428/407
4,735,906 A *  4/1988 Bastiaans ..................... 436/527
(Continued)

FOREIGN PATENT DOCUMENTS

GB  2 416 210 A  1/2006

OTHER PUBLICATIONS

International Search Report dated Apr. 18, 2012, as issued in corresponding International Patent Application No. PCT/GB2011/052105, filed Oct. 28, 2011—5 pages.
(Continued)

*Primary Examiner* — Brian J Sines
(74) *Attorney, Agent, or Firm* — Maier & Maier, PLLC

(57) ABSTRACT

An apparatus with a transducer having a first output signal and arranged to receive an electrical input. The transducer switches the first output signal between an ON and OFF state. The apparatus has a chemical sensing surface coupled to the transducer arranged to receive a chemical input. A signal generator oscillates one or more of said inputs to vary the switching point of the transducer. The oscillating input may be the chemical input and/or the electrical input. The output signal may be a pulse whose period ON or OFF is determined by the oscillating input modulated by the chemical input.

10 Claims, 5 Drawing Sheets

(51) Int. Cl.
*G01N 33/48* (2006.01)
*C12Q 1/68* (2006.01)
*G01N 27/414* (2006.01)
*G01N 27/44* (2006.01)

(58) Field of Classification Search
USPC ............ 422/68.1, 50, 82.02, 82.01, 83, 98;
436/43, 518, 524, 528, 532, 63, 149, 151;
435/283.1, 285.2, 287.1, 287.2, 287.7,
435/287.8, 287.9
See application file for complete search history.

(56) References Cited

U.S. PATENT DOCUMENTS

| | | | | |
|---|---|---|---|---|
| 4,847,193 | A | * | 7/1989 | Richards et al. ............ 435/6.19 |
| 4,874,499 | A | * | 10/1989 | Smith et al. ............ 204/403.03 |
| 5,220,836 | A | * | 6/1993 | Harms et al. ................... 73/702 |
| 6,235,488 | B1 | * | 5/2001 | Tom-Moy et al. ............ 435/7.5 |
| 6,977,180 | B2 | * | 12/2005 | Hellinga et al. ............. 436/518 |
| 7,686,929 | B2 | | 3/2010 | Toumazou et al. |
| 7,888,015 | B2 | | 2/2011 | Toumazou et al. |
| 8,114,591 | B2 | | 2/2012 | Toumazou et al. |
| 2005/0230245 | A1 | | 10/2005 | Morgenshtein et al. |
| 2010/0255595 | A1 | | 10/2010 | Toumazou et al. |
| 2011/0140703 | A1 | * | 6/2011 | Chiao et al. .................. 324/438 |
| 2011/0247932 | A1 | | 10/2011 | Sun et al. |
| 2014/0027295 | A1 | * | 1/2014 | Chiao et al. .................. 205/122 |

OTHER PUBLICATIONS

Dong-Che Li, et al., "CMOS Open-Gate Ion-Sensitive Field-Effect Transistors for Ultrasensitive Dopamine Detection", IEEE Transactions on Electron Devices, vol. 30, No. 10, pp. 2761-2767, Oct. 1, 2010.

Wong, W. et al., "PG-ISFET based DNA-logic for reaction monitoring", The Institute of Engineering and Technology Journal, Electronics Letters, vol. 46, No. 5, pp. 330-332, Mar. 4, 2010.

Wong, W. et al., "Towards ISFET based DNA logic for rapid nucleic acid detection", IEEE Sensors, pp. 1451-1454, Oct. 25, 2009.

W.S. Wan Zain, et al., A Bulk-Driven ISFET-Based Chemical Mixer, Biomedical Circuites and Systems Conference, pp. 134-137, Nov. 3, 2010.

Carlo Colombo, et al., "Coulometric micro-titrator with a ruthenium dioxide pH-electrode", Analytica Chimica Acta 412, pp. 69-75, Jan. 26, 2000.

* cited by examiner

US 9,683,260 B2

CHEMICAL SENSING DEVICE

RELATED APPLICATIONS

This is the U.S. national stage application which claims priority under 35 U.S.C. §371 to International Patent Application No.: PCT/GB2011/052105 filed on Oct. 28, 2011, which claims priority to Great Britain Patent Application No. 1018224.4 filed on Oct. 28, 2010, the disclosures of which are incorporated by to reference herein their entireties.

FIELD OF THE INVENTION

The present invention relates to devices for chemical sensing. In particular the invention may be used to provide a digital output signal dependent on the concentration of an ion in a fluid. The invention is applicable to nucleic acid identification and sequencing.

BACKGROUND

Previously publications have disclosed the ability of an ION Sensitive Field Effect Transistor (ISFET) to detect chemicals proximate the sensing surface. This may be used to determine the presence of a target analyte by detection of products of a chemical reaction. In one example, ISFETs can be used determine the identity of one or more portions of a nucleic acid template by detecting the change in pH resulting from nucleotide insertion at the end of a nucleic acid. Typically hydrogen ions (protons) are released during the reaction. The electrical signal strength of the ISFET depends on the amount of hydrogen ions released, which is expressed as an analogue output signal, which is either a voltage or current signal.

For large scale arrays of ISFETs, such as might be used in DNA sequencing, the inventors have appreciated that processing this analogue data requires enormous computing power and a bandwidth of gigabits/second.

In addition, the normal method requires accurate analogue readout circuitry, and is sensitive to the parasitic components, and environmental electrical noise. High accuracy and large-scale analogue systems limit the processing speed and integration ability; thereby constraining the detection efficiency and scalability. Moreover, high performance front-end interface circuitry consumes large amounts of system area and power, make on-chip data processing unrealistic.

The inventors propose herein a novel semiconductor and method that addresses one or more of the above deficiencies.

SUMMARY OF THE INVENTION

According to a first aspect of the invention there is provided a semiconductor device comprising a transducer having a first output signal and arranged to receive an electrical input. The transducer switches the first output signal between an ON and OFF state. The device comprises a chemical sensing surface coupled to the transducer arranged to receive a chemical input. A signal generator oscillates one or more of said inputs to varies the switching point of the transducer.

The oscillating input may be the chemical input and/or the electrical input.

The output signal may be a pulse whose period ON or OFF is determined by the oscillating input modulated by the chemical input.

The signal generator may comprise a titration electrode arranged to release or adsorb a chemical, which chemical affects a concentration of ions detected by the chemical sensing surface. The signal generator may further comprise a controller to provide an oscillating electrical current to the titration electrode.

Said chemical is preferably hydrogen ions or hydroxide ions.

The signal generator may oscillate the chemical input signal to switch the first output signal ON for a first period and OFF for a second period. The signal generator may also oscillate the electrical input signal to switch the first electrical output signal ON for a first period and OFF for a second period; further wherein the chemical input signal modulates the period of the first and second period.

The signal generator may provide an oscillating electrical input signal to a transistor comprised in the transducer at one of: a gate, a source, a drain, or a bulk.

The ions to be detected proximate the chemical sensing surface may provide the chemical input signal to bias the transducer to modulate the first output signal.

The transducer may comprise a first transistor of a first type connected to a second transistor of a second type to form a CMOS inverter. The chemical sensitive surface may be coupled to gates of the first and second transistors. The gate may be a floating gate.

The first electrical output signal may be provided to one or more further transistors to form a logic circuit.

The apparatus may further comprise a demodulator receiving the first electrical output signal, the demodulator providing a second digital output signal representing the magnitude of the chemical input signal.

The demodulator may be one of: a Phase Demodulator or Time to Digital Convertor (TDC).

The apparatus may further comprise an encoder connected to the second output signal, the encoder arranged to provide a third output signal comprising a 2-bit binary code.

Preferably, an oscillating waveform of the signal generator is provided as one of: a sawtooth wave, a sinusoidal wave, or a triangular wave.

According to a second aspect of the invention there is provided a method of determining one or more components of an analyte in a fluid using An apparatus according the first aspect, and comprising the steps of (i) providing the fluid to the chemical sensing surface; (ii) oscillating one or more of the inputs to provide a modulated first output signal; (iii) demodulating the modulated first output signal to provide a first data representing a first ion concentration; (iv) combining an analyte specific reagent with the fluid, whereby ions are produced if the reagent reacts with the analyte; (v) oscillating one or more of the inputs to provide a modulated first output signal; (vi) demodulating the modulated first output signal to provide a second data representing a second ion concentration; (vii) comparing the first data and second data to quantify a change in ion concentration; and then (viii) comparing the change in ion concentration with a threshold to determine whether the reagent reacted with the analyte to determine a component of the analyte.

The method may further comprise demodulating the first and second modulated output signals to provide first and second digital output signals representing an ion concentration and then comparing the first and second digital output signals to quantify a change in ion concentration of the fluid.

The method may also further comprise removing the extant reagent from the fluid after (iv). Indeed, it is also preferred that at least (ii) to (vi) are repeated to determine further components of the analyte.

The analyte is preferably a nucleic acid template to be sequenced and the reagent is a known type of nucleotide. It is preferred, therefore, that the ion concentration changes depending on whether the nucleotide is inserted onto the nucleic acid template.

The change in ion concentration ideally correlate to the number of nucleotide bases inserted onto the nucleic acid template.

The encoder may provide a 2-bit binary code representing the type of nucleotide inserted.

According to a third aspect of the invention there is provided a method of measuring ion concentration in a buffered fluid, the method comprising the steps of: (i) monitoring an electrical output signal from an ISFET exposed to the fluid; (ii) releasing or adsorbing a chemical from a titration electrode to the fluid to change said ion concentration until the output signal reaches a predetermined threshold; and (iii) determining the quantity of chemical released or adsorbed.

The method may determine the initial ion concentration from knowledge of the buffer capacity and amount of chemical released or adsorbed. The method may, therefore, further comprise (iv) determining the initial ion concentration from knowledge of the buffer capacity and amount of chemical released or adsorbed. It may also further comprise repeating parts (ii) and (iii) at two different times or with different fluids and then:

(iv) determining the difference in initial ion concentration from knowledge of the difference in amount of chemical released or adsorbed in each part (ii), wherein the buffer capacity before each part (ii) is substantially the same.

The method may repeat steps (ii) and (iii) at two different times or with different fluids and then (iv) determine the difference in initial ion concentration from knowledge of the difference in amount of chemical released or adsorbed in each step (ii), wherein the buffer capacity before each step (ii) is substantially the same. The method may also comprise undoing the effects of step (ii) by adsorbing to or releasing from the titration electrode a substantially equal quantity of said chemical from or to the fluid.

Thus, the method may preferably further comprise undoing or partially reversing the effects of part (ii) by adsorbing to or releasing from the titration electrode a substantially equal quantity of said chemical from or to the fluid. The method may, therefore, also preferably further comprise undoing or partially reversing the effects of part (ii) by adsorbing to or releasing from a second titration electrode a substantially equal quantity of a second chemical from or to the fluid.

It is preferred that the period of part (ii) is greater than 2 seconds, preferably greater than 5 seconds, 10 seconds, or 30 seconds.

It is also preferred that the period of part (ii) is less than 200 seconds, preferably less than 100 seconds, 60 seconds, or 50 seconds.

A relationship between said output signal and ion concentration is preferably known.

Preferably, the threshold is one of: a predetermined change in the output signal; a predetermined rate of change in the output signal; or a state of the output signal changing from ON to OFF or vice versa.

The ion concentration changes are preferably due to a chemical reaction. The amount of chemical released or absorbed is preferably determined as the total electric charge provided by a controller to the titration electrode.

The invention provides a simplified architecture for processing an ISFET signal, which increases the integration ability of sensor and processing into a single chip. The inherent analogue to digital conversion of preferred embodiments not only removes the need for several steps for signal conditioning and analogue processing but also reduces electrical noise associated with these steps compared to prior art devices.

Thus, in a further aspect, there is provided an array of apparatuses discussed above. The array may comprise a multiplexer connected to each device to select which first output signal is to be demodulated. Preferably, the array is of apparatuses wherein said transducer comprises a first transistor of a first type connected to a second transistor of a second type to form a CMOS inverter. Preferably, said array comprises a multiplexer connected to each said second transistor to activate or deactivate individual devices. The array may further comprise a CDMA processor to encode output signal from each device, preferably enabling said output signals to be transmitted on a single channel.

BRIEF DESCRIPTION OF THE DRAWINGS

Specific embodiments of the invention will now be described by way of example only with reference to the accompanying figures, in which.

DETAILED DESCRIPTION

In a system comprising the invention there will typically be a semiconductor substrate housing the sensor and signal processing, overlaid by a substrate containing fluidic channels and one or more chambers. The chambers contain a fluid which has an ion concentration to be measured. The ion concentration may be constant or may be changing. The change may be a result of a chemical reaction releasing or absorbing the ions. The limit of detection of such a system is governed by a) the amount of buffer in the fluid which masks changes in ion concentration and b) the electrical characteristics of the transistor which requires the ionic charges to create an electric field to permit electric current to flow and be detected. These can be seen as thresholds to be exceeded. In the present invention a controlled oscillating signal is provided to the system, which in combination with the chemical/ionic signal exceeds one or both of these thresholds to provide a detectable output signal. The effect of the controlled signal is subtracted from the output signal to determine the effect of the chemical signal contribution. By oscillating the controlled signal the net effect over time to the system is zero. The oscillating signal is ideally continuously varying over a portion of the period such that the point at which the threshold is crossed can be determined.

In one embodiment, the oscillating signal is a chemical provided to the fluid to change the ion concentration within the buffer. In another embodiment, the oscillating signal is an electrical signal provided to the sensor transducer to change the electrical operating point. Combinations of these embodiments are envisaged and within the scope of the invention.

In such a system the chemical signal can be regarded as modulating the output signal and doing so in an efficient form for data processing. Ideally the chemical concentration is converted to a digital signal to be further processed. Processing of this signal may be performed in hardware or software.

Electrical Oscillation

Figure 1:
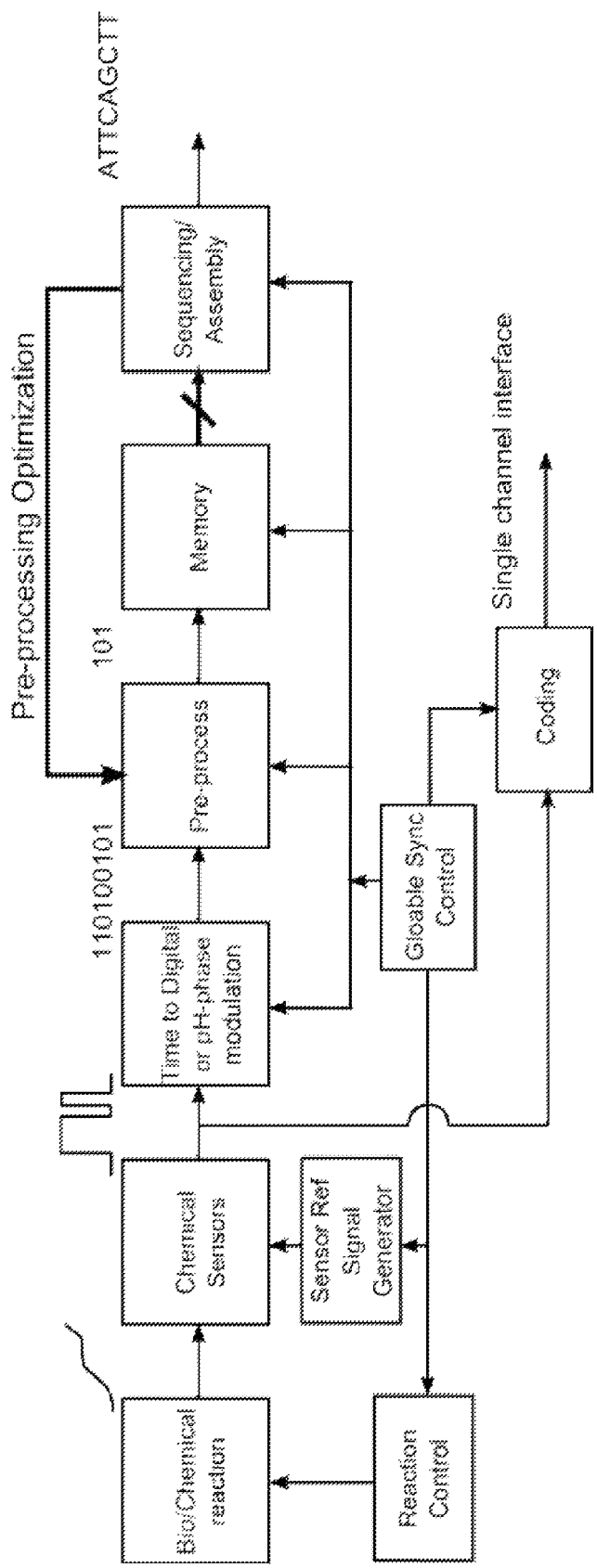
FIG. 1 is a block diagram of a system of a preferred embodiment.

A block diagram of an exemplary system is shown in FIG. 1. A fluid sample, which contains a concentration of an analyte (including zero concentration where the analyte is absent from the sample), is in contact with a chemical sensing surface of an ISFET that converts the concentration of the analyte into an analogue electrical signal. A transducer converts the chemical signal into an analogue signal. The transducer is connected to an oscillating signal input. The chemical signal and oscillating signal combine to produce an oscillating output signal. If the transducer comprises an ISFET forming part of a CMOS inverter, the transducer will turn on and off to produce a pulsed output signal as shown. The analogue chemical signal contributes to modulate the output signal such that the phase shifts or pulse width changes. This change represents the chemical concentration. Then a Time to Digital Converter or Phase Demodulator decodes the pulse signal and outputs a digital signal. The contribution from the oscillating input signal can be deducted to leave the net chemical contribution. These signals may be pre-processed and stored in memory. The Time to Digital Converter may be of the types described in:

Jianjun Yu et al, 12-Bit Vernier Ring Time-to-Digital Converter in 0.13 um CMOS Technology, IEEE JOURNAL OF SOLID-STATE CIRCUITS, VOL. 45, NO. 4, April 2010; or Gordon W. Roberts, *A Brief Introduction to Time-to-Digital Digital-to-Time Converters*, IEEE TRANSACTIONS ON CIRCUITS AND SYSTEMS II: EXPRESS BRIEFS, VOL. 57, NO. 3, March 2010.

As discussed further below the signals may represent a series of nucleotide incorporation reaction of a fragmented DNA strand, in which case the signals are further processed to sequence the complete DNA by mapping algorithm units.

Figure 2:
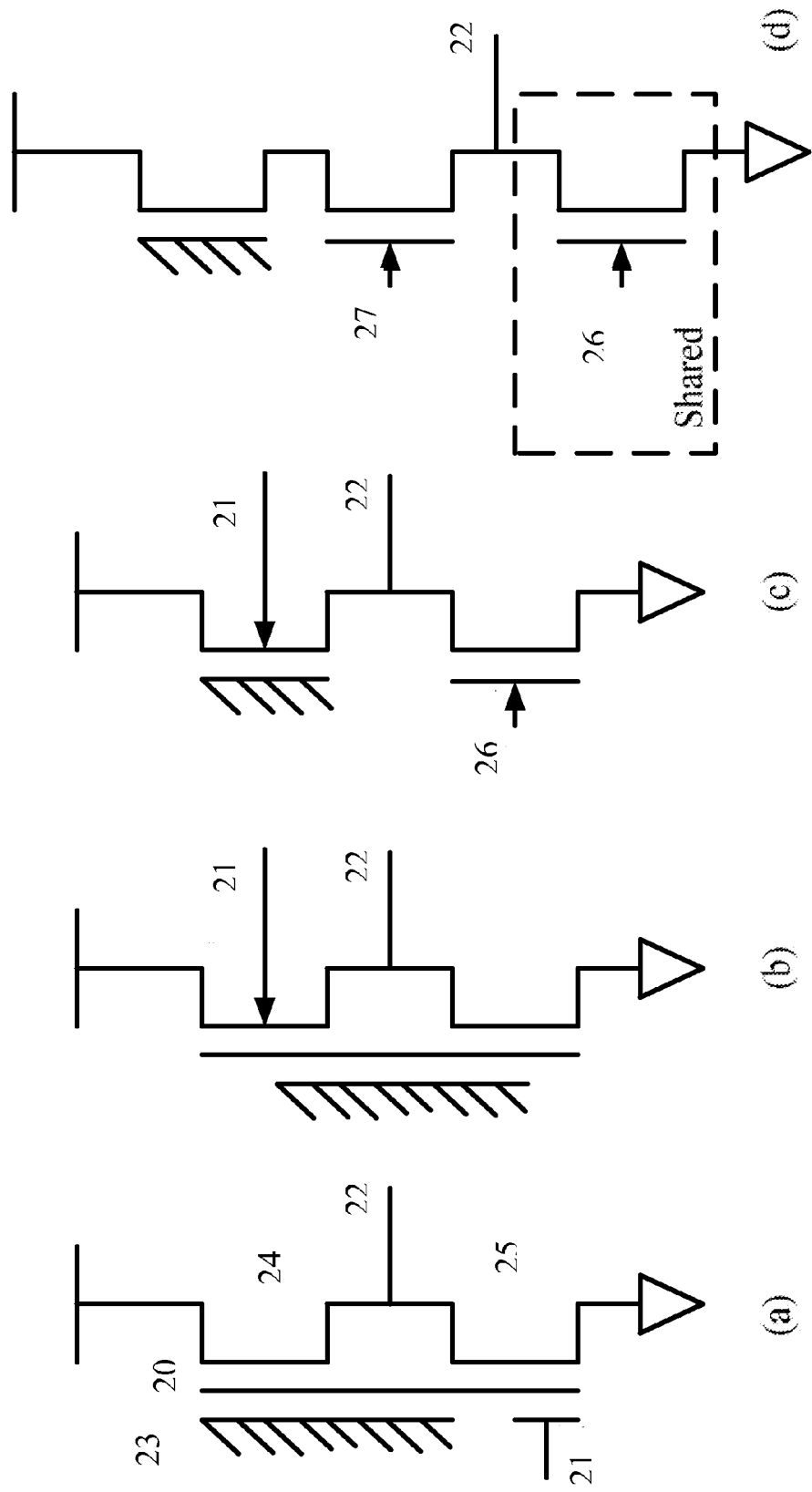
FIG. 2 shows four schematic arrangements of transducers.

In one embodiment, depicted in FIG. 2a, a chemical sensing layer 23 is coupled to a floating gate 20 shared by two transistors (24 and 25) arranged as an inverter. An output 22 is connected to the drains. The voltage on the gate will have the effect of turning one transistor on and the other off such that the output is inherently digital. For further reference on this arrangement and operation see application PCT/IB2011/002376. Further device approaches can be extended to 2(b) or 2(c) using bulk input modulation or 2(d) using pseudo CMOS logic.

By connecting a signal generator to a terminal of a transistor, the transistor can be biased such that the output is of a predetermined form to enable a chemical signal to modulate the output as desired. The oscillating signal may be provided by a signal generator in the semiconductor substrate capacitively coupled to the gate of a transistor. For example an oscillating signal from the signal generator could electrically bias the transistor to turn on and off for set periods, with any chemical signal adding to the bias to modulate those periods. Typically the voltage of the oscillation will vary continually between Vss and Vdd. For example the signal may vary from 0V to 3.3V. Sawtooth, sinusoidal, or triangular waveforms are preferred. The frequency of the oscillating signal is dictated by factors such as the frequency scanning the array, the time interval of a chemical reaction being observed, and the resolution required for the digital output signal to detect a change in the ion concentration.

The ISFET inverter can be driven by common or individual signal at a specific frequency, and the output signal phase will be modulated by the hydrogen or other target ion concentration. The output signal, which essentially becomes a chemical modulated digital signal, dramatically simplifies the readout and processing blocks, and is immune to most electrical noise.

The number of transducers and chambers will depend on the application but in preferred embodiments there will be an array of more than 10, more than 100, more than 1000, more than 10,000, more than 100,000, or more than a 1,000,000. In applications requiring more transducers and the chamber size will typically be smaller. In preferred embodiments, the chamber volume is less than 1 mL, less than 10 uL, less than 100 nL, less than 30 nL, less than 1 nL, or less than 100 pL.

A Code division multiple access (CDMA) technique may also be incorporated in the system to encode the data from each transducer pixel in an array of transducers, allowing all the pixel data to be sent down a single channel.

Due to its simplified readout system, methods and devices of the invention can be widely implemented in different technologies, such as a discrete glass ISFET or a CMOS based ISFET. For large scale integration purposes, CMOS based ISFETs are preferable and are described below to further explain the implementation.

In contrast to the embodiment of FIG. 2(a), the oscillating signal may be connected to the bulk as shown in FIG. 2(b). FIG. 2(c) shows a third embodiment for a row of devices wherein the chemical sensing surface is coupled to a single FET and the second FET of the inverter is switched on and off by a row-select signal 26. For a two-dimensional array of transducers, the embodiment shown in FIG. 2(d) is desirable.

In FIG. 2(d) a single pixel comprises of a sensing transistor, a pass transistor, and a selection transistor. The selection transistor can be used to control the final output 22 in a single row or column. Either of the row select control 26 or the column select control 27 can be connected to the oscillating signal. Since the output signal will be digital, the transistor size can be further scaled down to sub-micron, and limited by the chemical setup only. In any of these configurations, the signal loss and distortion is negligible since a digital output is used.

Figure 3:
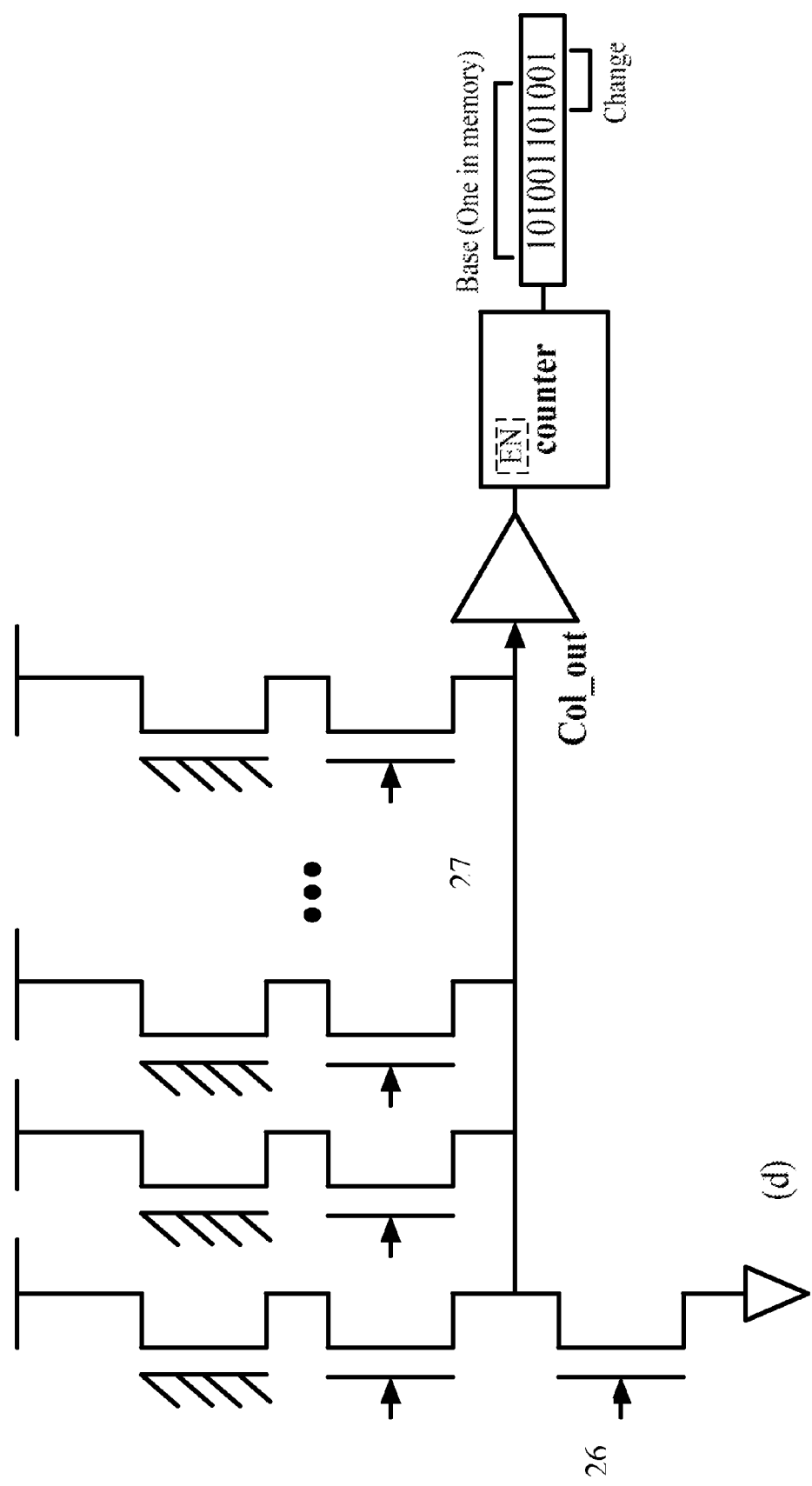
FIG. 3 is a schematic of a readout circuit.

All the transducer pixels can share one buffer and one front-end readout. However, in order to further speed up the processing, transducers in one row (or column) can share one readout channel. In each readout channel, the digital pulses are buffered using a digital inverter (or bit buffer_. FIG. 3 shows a counter system to readout the phase-modulated pulse signal and output a digital sequence.

The output of a time to digital converter will be truncated to a short length representing the change of chemical signal. This configuration can reduce the data handled and memory required. For instance, the entire output, which might normally have 12-bits resolution, will be reduced to 4 bits and stored into memory. The base line will be treated as common signal and stored as well. Therefore for each pixel, the maximum data required is the base count times 4 bits plus 10 bits common mode signal.

Application to Nucleic Acid Detection and Identification

In the field of genetic testing, it is desirable to identify one or more nucleotides of a nucleic acid (such as DNA and RNA). Typically a single strand of nucleic acid is annealed with a probe up to or including a point on the nucleic acid to be identified. Nucleotides will become incorporated to the 3' end of the probe to extend the chain. This incorporation reaction has been shown to release hydrogen ions which are detectable by an ISFET with a suitably treated sensing surface. For example the surface may be Silicon Nitride, Silicon Dioxide, Tantalum Oxide, or others shown to have sensitivity to hydrogen ions.

A nucleotide will only become incorporated if it is complementary to the nucleotide opposite. By correlating the known chemical compound added (e.g. the type of nucleotide dATP, dNTP, dTTP, dGTP, or allele specific probe) to a change (or lack thereof) in output signal, a nucleotide at a point of interest on the nucleic acid can be identified. Details of such application and implementation have been described in U.S. patent application Ser. No. 11/625,844 and U.S. Pat. No. 7,686,929 and U.S. Pat. No. 7,888,015, incorporated herein by reference.

Sequencing

As an extension to the identification of a single nucleotide base in a nucleic acid, it is desirable to identify a sequence of tens to hundreds of nucleotide bases.

In one method known as the shooting gun method, a whole chain of DNA is cut into small pieces, and copied to increase detection redundancy. The pieces are divided amongst an array of sensor pixels. Therefore every pixel data represents a copy of a small piece of DNA. Identifying the overlap of base sequences, in other words data similarity in memory, provides the entire DNA base sequence. This comparison can be implemented by digital logic, i.e. XOR, AND, NOR, NAND etc. A digital processing block can concatenate the sequence based on the comparison results. The processing can be performed in parallel with the sensing function, with the results of mapping feedback into the pre-process part, to reduce the computation complexity and memory requirement.

Results

Figure 4:
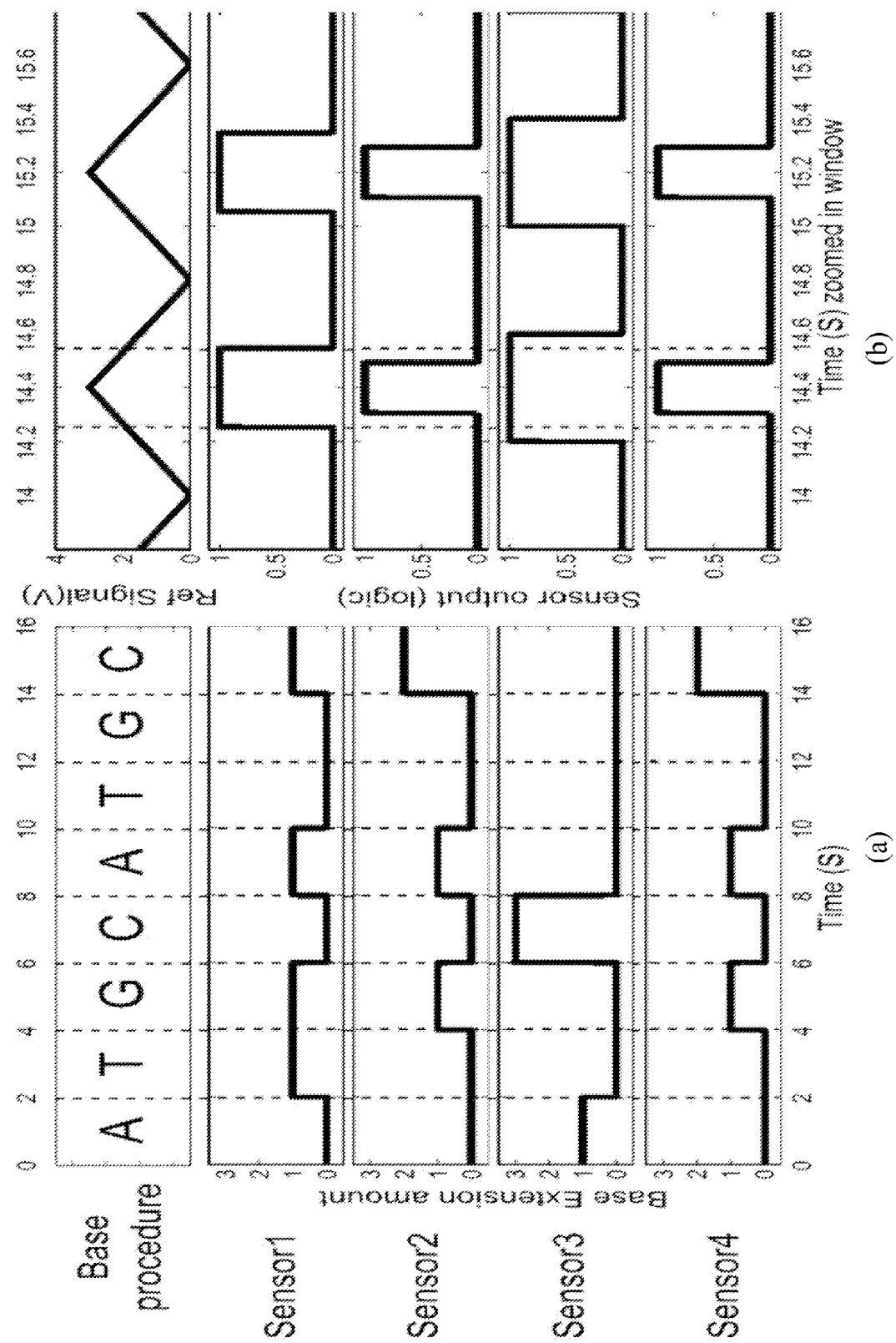
FIG. 4 shows graphs of output signals of nucleic acid reactions.

Simulation results based on a 6-base long DNA is shown in FIG. 4, wherein the graphs show (a) the base calling order and base extension at each of four sensors over the entire reaction period (16 seconds) and (b) the oscillating reference signal and modulated output signals for each sensor over a single reaction (2 seconds).

An exemplary simulation of a method of sequencing is described below and shown in FIG. 4. The set up parameters and outputs are given in the table below showing the simplified results of the processing. A nucleic acid to be identified (TGACCC) is copied and cut up to provide four fragments (Fragment 1, 2, 3, 4) with one fragment placed in one chamber, each chamber having one sensor (Sensor 1, 2, 3, 4). There would normally be millions of identical copies of a given fragment in a chamber. A probe is attached to each fragment up to but not including the bases shown. The probe is not shown for simplicity of understanding.

The order of nucleotides added (the bases call order) is dATP, dCTP, dTTP, and dGTP (A, C, T, G), which is repeated until each fragment is fully extended. The fluid is initially set to pH7 and is reset to pH7 after every base is added.

Every 2 seconds in this case, a new base will be added to each chamber in the order given above. Extension will occur if the added base is complementary to the fragment at the base opposite to release hydrogen ions. For each base extension, the released hydrogen will induce a specific pH drop, in our case, −0.2 pH per base extended. This pH will be directly reflected by the output signal with a modulated width or phase correlating to the pH change (FIG. 4(b)). Note that in the case where an inverter is used, more base extension, leading to greater ion release, reduces the ON period of the output signal.

The oscillating input signal to the sensor is a triangular wave as shown in FIG. 4(b), having a frequency higher than the rate of base addition, preferably higher than the rate of the smallest change to be detected.

The amount of pH change can be extracted from this signal by removing the initial pulse width (i.e. at pH 7). This is converted to the number of bases that were extended by dividing the pH change by the rate of change per base (0.2 pH/base in our case). See the Sensor output in FIG. 4(a). In reality the pH change is not linear for each base extended nor is the change instantaneous and stable over the reaction.

By correlating the addition of the known base with the count of extension, the sequence of each fragment can be identified. The base of each fragment can be represented by a 2-bit binary code provided by an encoder (e.g. 00=A, 01=T, 10=G, 11=C). Finally the identified fragments are reassembled using known mapping techniques (not shown):

|  | Nucleic Acid Template | T | G | A | C | C | C |  |  |
|---|---|---|---|---|---|---|---|---|---|
|  | BASE Call Order | A | C | T | G |  | Repeat | . | . . |
|  | Fragment 1 | T | G | A | C |  |  |  |  |
|  | Fragment 2 | G | A | C | C |  |  |  |  |
|  | Fragment 3 | A | C | C | C |  |  |  |  |
|  | Fragment 4 | G | A | C | C |  |  |  |  |
| Extension Count | Sensor1 | 0 | 1 | 1 | 0 | 1 | 0 | 0 | 1 |
|  | Sensor2 | 0 | 0 | 1 | 0 | 1 | 0 | 0 | 2 |
|  | Sensor3 | 1 | 0 | 0 | 3 | 0 | 0 | 0 | 0 |
|  | Sensor4 | 0 | 0 | 1 | 0 | 1 | 0 | 0 | 2 |

For example, during a 4 second period of base addition, the pH change from an extension reaction may last 1 second. To measure the change, capturing the peak and width of the pH change, the pH is sampled 10 times over the 1 second period. The width of the ON periods will vary over the 4 second reaction window. The quantification of base extension may involve a complex algorithm looking at the minimum pulse width, average pulse width, sum of pulse widths, etc.

It can be seen that the output sequence can be easily derived from this scheme.

Advantageous of preferred embodiments of a system are:
  by using a novel configuration of ISFETs, the total transistor count for a single detection pixel can be reduced to two (including selection transistor).
  no analogue processing circuitry is necessary.
  Output is immune to conversion time and most electrical noise induced by the digital processing circuit.
  Transistor size can be reduced further since digital logic is adopted and transistor mismatch can be neglected.
  The processing and memory blocks can be integrated into a single chip.
  Since all detection is synchronized, sequencing and comparison can be triggered accurately for all the pixels. Sequencing can be performed concurrently with the reaction, dramatically reducing the processing time and improving the processing accuracy.
  In one embodiment, the reference signal is reset before each nucleotide insertion step to compensate for any background ion concentration (for example the concentration remaining from the previous insertion step). The reset reference signal together with the background chemical signal thus produces a consistent pre-insertion reference output signal, any subsequent modulation to the output signal representing the concentration change due to the current nucleotide insertion step.

In addition to sequencing a nucleic acid, the device may be used to identify other chemicals. For example, a complex molecule having several identifiable elements of varying types can be identified be using a step-wise (or repeated) reaction with analyte specific reagents. The digital output will identify the exact type of the molecule.

Chemical Oscillation

As discussed above, in one embodiment the chemical input to the system may be varied by a controlled chemical signal such that the initial ion concentration acts to modulate the output signal. The combined chemical signal can be swept through a range to examine the a) ion concentration within the buffer and b) examine the electrical operating point of the transistor (sub-threshold, linear, saturation). The former is useful when the initial ion concentration is within the buffer capacity such that any small changes will be masked by the buffer. The latter may be operated as described above with an inverter to create an output pulse whose width is modulated by the initial ion concentration. The two effects may be combined such that adding titrant moves the ion concentration operating point beyond the buffer capacity and also crosses a switching point of the inverter.

Figure 5:
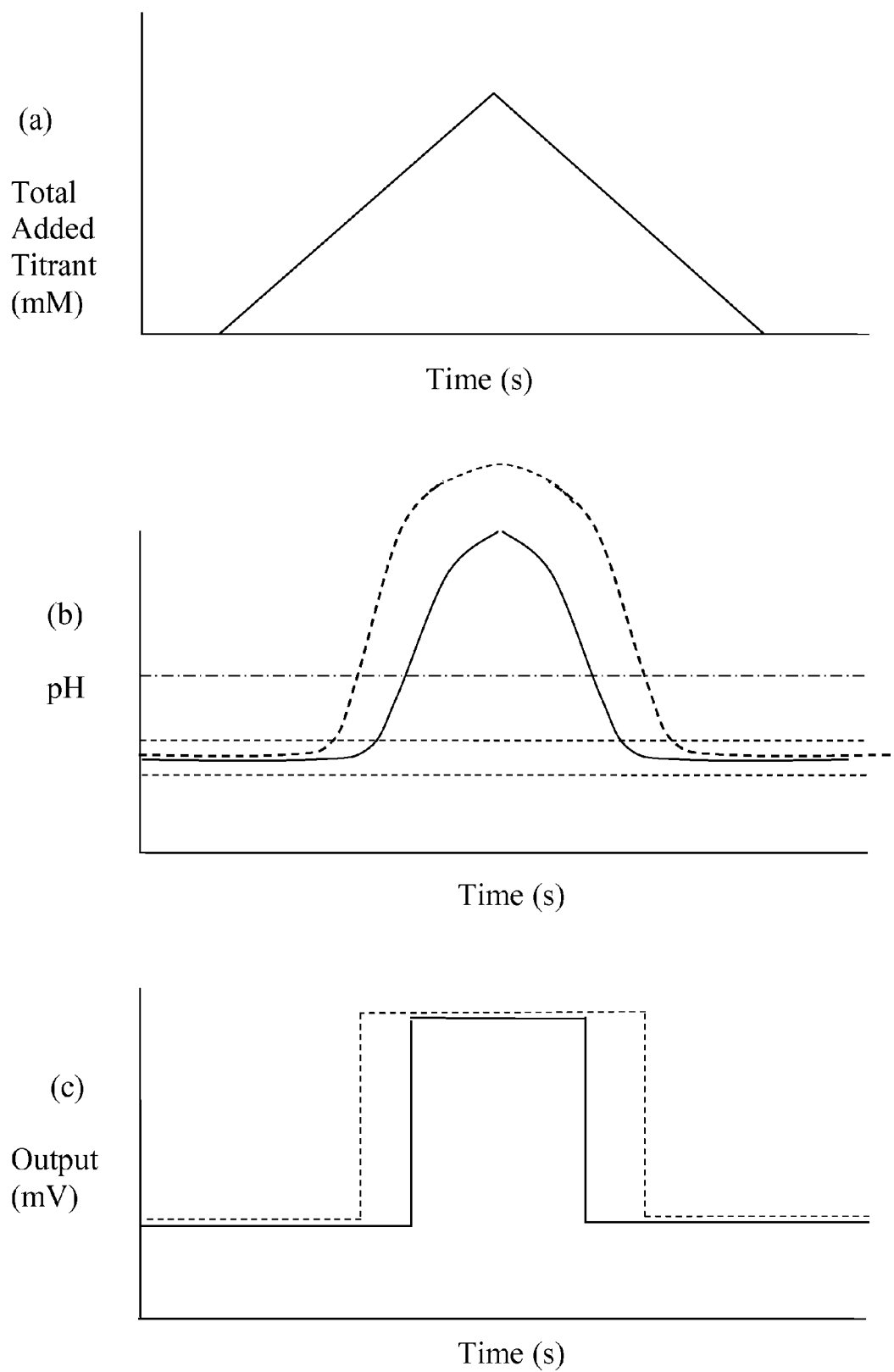
FIG. 5. shows graphs of input and output signals for a system having an oscillating chemical input.

The effect is demonstrated in FIG. 5. In graph 5(a) a controlled quantity of titrant is added to the fluid over a first period and the removed over a second period. The net chemical effect on the system is thus zero. In graph 5(b) the pH of two cases are plotted over the same periods. In the first case (solid line), the hydrogen ion concentration is small compared to the buffer capacity and so takes a long time before there is a detectable pH change. In the second case (dashed line), the hydrogen ion concentration is large compared to the buffer capacity and so takes less time before there is a detectable pH change. As the ion concentration exceeds the buffer capacity the rate of pH change per quantity of titrant added increases. This is seen as a steeper slope after the horizontal buffer lines.

The initial ion concentration can be measured by the time (amount of titrant added) until the slope reaches a threshold slope or the pH change exceeds a threshold. This is clearly an inverse relationship between time and concentration. The relationship may be determined by a model of the chemical system or determined empirically. The relationship may be stored as a look-up table in memory.

The pH in graph 5(b) could be used to produce an analogue output signal from the ISFET to be detected and measured. It is also possible to form an ion sensitive switch as described above, where two FETs are arranged as an inverter biased to switch when the ion concentration exceeds a threshold (identified as the upper horizontal line in FIG. 5(b). The output will thus be ON or OFF, wherein the period ON depends on the initial ion concentration as shown in FIG. 5(c).

The titration reaction is naturally slow and so the oscillation period in preferred embodiments is greater than 2 seconds, preferably greater than 5 seconds, 10 seconds, or 30 seconds. However, the period should not be so long as to miss changes in the ion concentration or slow down detection time. Thus in preferred embodiments, the oscillation period is less than 200 seconds, preferably less than 100 seconds, 60 seconds, or 50 seconds.

A threshold may be reached when the concentration of titrated ions (T) plus initial ions (I) is greater than the buffer capacity (B).

In cases where a change in ion concentration is to be detected, the initial ion concentration is determined at a first time using the steps discussed above and illustrated in FIG. 5. The steps are repeated at a second time to determine if more or less titrant was needed to reach the threshold.

The threshold is reached at time 1 when:

$$T1+I1>B;$$

The threshold is reached at time 2 when:
T2+I2>B; and thus (regardless of the buffer capacity (which may be unknown)):

$$(I1-I2)=\Delta I=T2-T1$$

Thus the change in initial ion concentration is known from the amount of titration required at each time to reach the threshold.

In cases where the initial ion concentration is to be measured only once, titration may be unidirectional, such that titrant is added or removed in a first period, but the effect is not reversed in a second period. To measure the absolute initial ion concentration, it is necessary to know the buffer capacity of the fluid and the amount of titrant added to exceed the capacity to reach a threshold (e.g. slope or change):

i.e. $B-T=I.$

In either case, the titration electrode may be operated to add or release chemicals, which chemicals affect the ion concentration to be detected. The effect may be to increase or decrease ion concentration from the initial concentration.

The titrant added need not be a predetermined amount, but may rather be added until one of the thresholds is reached. In this case the amount added is calculated.

Titration may be achieved by exposing a titration electrode to the fluid. The electrode is connected to a controller which provides a controlled amount of electric current. Calculating the integral of current over time results in a known quantity of charge, which is proportional to the quantity of titrant released or adsorbed to the electrode. The titration electrode may be of the type described in B. van der Schoot et al., *Titration-on-a-chip, chemical sensor-actuator systems from idea to commercial product*, Sensors and Actuators B 105 (2005) 88-95.

The titration reaction at an electrode with a negative charge may by expressed as:

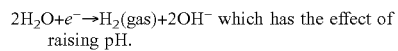
$2H_2O+e^- \rightarrow H_2(gas)+2OH^-$ which has the effect of raising pH.

The titration reaction at an electrode with a positive charge may by expressed as:

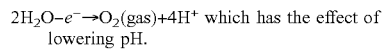
$2H_2O-e^- \rightarrow O_2(gas)+4H^+$ which has the effect of lowering pH.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. For example, references to connections may be made directly or indirectly, as appropriate. Each feature disclosed or illustrated in the present specification may be incorporated in the invention, whether alone or in any appropriate combination with any other feature disclosed or illustrated herein.

The invention claimed is:

1. An apparatus comprising:
    a transducer for providing a first electrical output signal and arranged to receive an electrical input signal, the transducer switching the first electrical output signal between an ON and OFF state;
    a chemical sensing surface coupled to the transducer for receiving a chemical input signal; and
    a signal generator for oscillating one or more of said input signals to vary the switching point of the transducer; wherein the signal generator provides an oscillating electrical input signal to a transistor comprised in the transducer at one of: a gate, a source, a drain, or a bulk.

2. An apparatus according to claim 1, wherein the signal generator comprises a titration electrode arranged to release or adsorb a chemical, which chemical affects a concentration of ions detected by the chemical sensing surface.

3. An apparatus according to claim 2, wherein the signal generator further comprises a controller to provide an oscillating electrical current to the titration electrode.

4. An apparatus according to claim 1, wherein the signal generator oscillates the chemical input signal to switch the first output signal ON for a first period and OFF for a second period.

5. An apparatus according to claim 1, wherein the signal generator oscillates the electrical input signal to switch the first electrical output signal ON for a first period and OFF for a second period; further wherein the chemical input signal modulates the period of the first and second period.

6. An apparatus according to claim 1, wherein said transducer comprises a first transistor of a first type connected to a second transistor of a second type to form a CMOS inverter.

7. An apparatus according to claim 1, wherein the first electrical output signal is provided to one or more further transistors to form a logic circuit.

8. An apparatus according to claim 1, further comprising a demodulator receiving the first electrical output signal, the demodulator providing a second digital output signal representing the magnitude of the chemical input signal.

9. An apparatus according to claim 8, further comprising an encoder connected to the second output signal, the encoder arranged to provide a third output signal comprising a 2-bit binary code.

10. An apparatus according to claim 1, wherein an array of apparatuses is formed and a multiplexer is connected to each device in the array to select which first output signal is to be demodulated.

* * * * *